United States Patent [19]

Weedon et al.

[11] Patent Number: 5,499,281

[45] Date of Patent: Mar. 12, 1996

[54] APPARATUS FOR SHIELDING AND GROUNDING X-RAY DETECTORS OF A CT SCANNER

[75] Inventors: Hans Weedon, Salem; John Dobbs, Hamilton, both of Mass.

[73] Assignee: Analogic Corporation, Peabody, Mass.

[21] Appl. No.: 316,922

[22] Filed: Oct. 3, 1994

[51] Int. Cl.⁶ ........................................................ A61B 6/00
[52] U.S. Cl. ............................................ 378/19; 378/98.8
[58] Field of Search .................................. 378/4, 19, 15, 378/98, 98.8

[56] References Cited

U.S. PATENT DOCUMENTS

| 4,345,156 | 8/1982 | Ishikawa et al. | 378/19 |
| 4,843,618 | 6/1989 | Best et al. | 378/4 |
| 5,323,439 | 6/1994 | Nobuta et al. | 378/19 |

*Primary Examiner*—David P. Porta
*Assistant Examiner*—Don Wong
*Attorney, Agent, or Firm*—Lappin & Kusmer

[57] ABSTRACT

The invention provides an apparatus for shielding and grounding an x-ray detector assembly which is thereby substantially protected from pickup and microphonics. The apparatus includes an electrically conductive enclosure substantially enclosing the detector assembly and connected to the ground plane of the data acquisition system (DAS) independently of the signal and return paths between the detector assembly and the DAS.

20 Claims, 3 Drawing Sheets

APPARATUS FOR SHIELDING AND GROUNDING X-RAY DETECTORS OF A CT SCANNER

FIELD OF THE INVENTION

This invention relates generally to x-ray detectors, and more particularly to shielding and grounding sensitive x-ray detector assemblies in electrically noisy environments, such as a CT scanner.

BACKGROUND OF THE INVENTION

In most known CT scanners, which typically include/an array of x-ray detectors, electrical noise can significantly degrade performance of the detectors, and therefore degrade the overall performance of the CT scanner. Consequently, much effort is spent finding the sources of such electrical noise, and developing ways to eliminate the effects of electrical noise within the CT scanner.

For example, in a CT scanner having an array of semiconductor x-ray detectors, the typical detector comprises a crystal for converting x-ray photons into visible light photons, and a photodiode for converting the visible light photons into extremely low-amplitude (on the order of picoamperes to nanoamperes) electrical currents representative of the x-ray flux incident on the detector. The extremely low-amplitude currents are transmitted via an array of respective conductors to a data acquisition system (DAS) for signal processing.

However, the extremely low-amplitude currents are vulnerable to interference when they are exposed to sources of low-level ambient electrical noise. Such noise can be caused by minute motions of the detector, called microphonics, which induce noise via the triboelectric effect. Noise can also be caused by small ambient voltage fluctuations that produce undesirable electrical interference often referred to as pickup.

Each detector and the DAS must be grounded. It is known to use the return lines of the detectors to connect the detectors to the system ground, as shown in FIG. 2 and described in greater detail hereinafter. However, large currents flowing in the system ground can produce noise, with voltage fluctuations on the order of millivolts not being unusual. Thus, grounding a detector to the system ground via a return line can expose the detector to undesirable electrical noise. In addition, voltage fluctuations on the mounting structure of the detectors can also subject the detector to undesirable pickup.

Moreover, there are signal sources outside the detectors that can capacitively couple to the photodiodes of the detectors to produce currents going back to the input of the DAS via the return lines of the detectors, thereby creating a (usually AC) potential differential across the return lines of the detectors and DAS ground. Although the potential difference is small, e.g., typically on the order of millivolts, it can adversely affect the performance of a sensitive instrument, such as a CT scanner.

OBJECTS OF THE INVENTION

It is a general object of the present invention to provide an apparatus for shielding and grounding sensitive x-ray detector assemblies in electrically noisy environments, such as a CT scanner, that significantly overcomes the problems of the prior art.

A more specific object of the present invention is to electrically isolate one or more x-ray detectors of a CT scanner, and their associated signal and return lines.

Another object of the invention is to prevent ambient pickup from corrupting signals provided by one or more x-ray detectors of a CT scanner, while also protecting each x-ray detector from ambient light.

Another object of the invention is to ameliorate the effects of microphonics in a CT scanner.

Other objects of the present invention will in part be suggested and will in part appear hereinafter. The invention accordingly comprises the apparatus possessing the construction, combination of elements, and arrangement of parts, all which are exemplified in the following derailed disclosure and the scope of the application, all of which will be indicated in the claims.

SUMMARY OF THE INVENTION

The principles of the present invention relate to a CT scan system comprising an X-ray detector assembly having signal and return paths respectively electrically connecting the detector assembly to the signal input and ground plane (defining system ground) of the DAS. In accordance with the present invention, electrically conductive shielding means, preferably in the form of an electrically conductive enclosure, i.e., a Faraday shield or cage, substantially surrounds or envelops the x-ray detector assembly, and a conductive path, separate from the return path of the detector, connects the shielding means to the ground plane of the DAS. This prevents any mixing of currents picked up by the electrically conductive enclosure with the signals generated by the detector, a feature which is especially advantageous where the currents flowing to and from the enclosure on its return line, due to noise from microphonics and pick-up, can be several orders of magnitude higher than the output currents of each detector of the detector assembly. The return path between the enclosure enveloping the detector assembly and the ground plane of the DAS also shields the signal and return paths of the apparatus. There are no voltage fluctuations with respect to the DAS in the shield or the return path since it is grounded at the DAS. Voltage fluctuations in the environment induce charges on the shield which cause currents to flow, but no significant voltages are induced.

BRIEF DESCRIPTION OF THE DRAWINGS

The invention will be more fully understood from the following detailed description, in conjunction with the accompanying figures, wherein.

DETAILED DESCRIPTION OF THE DRAWINGS

Figure 1:
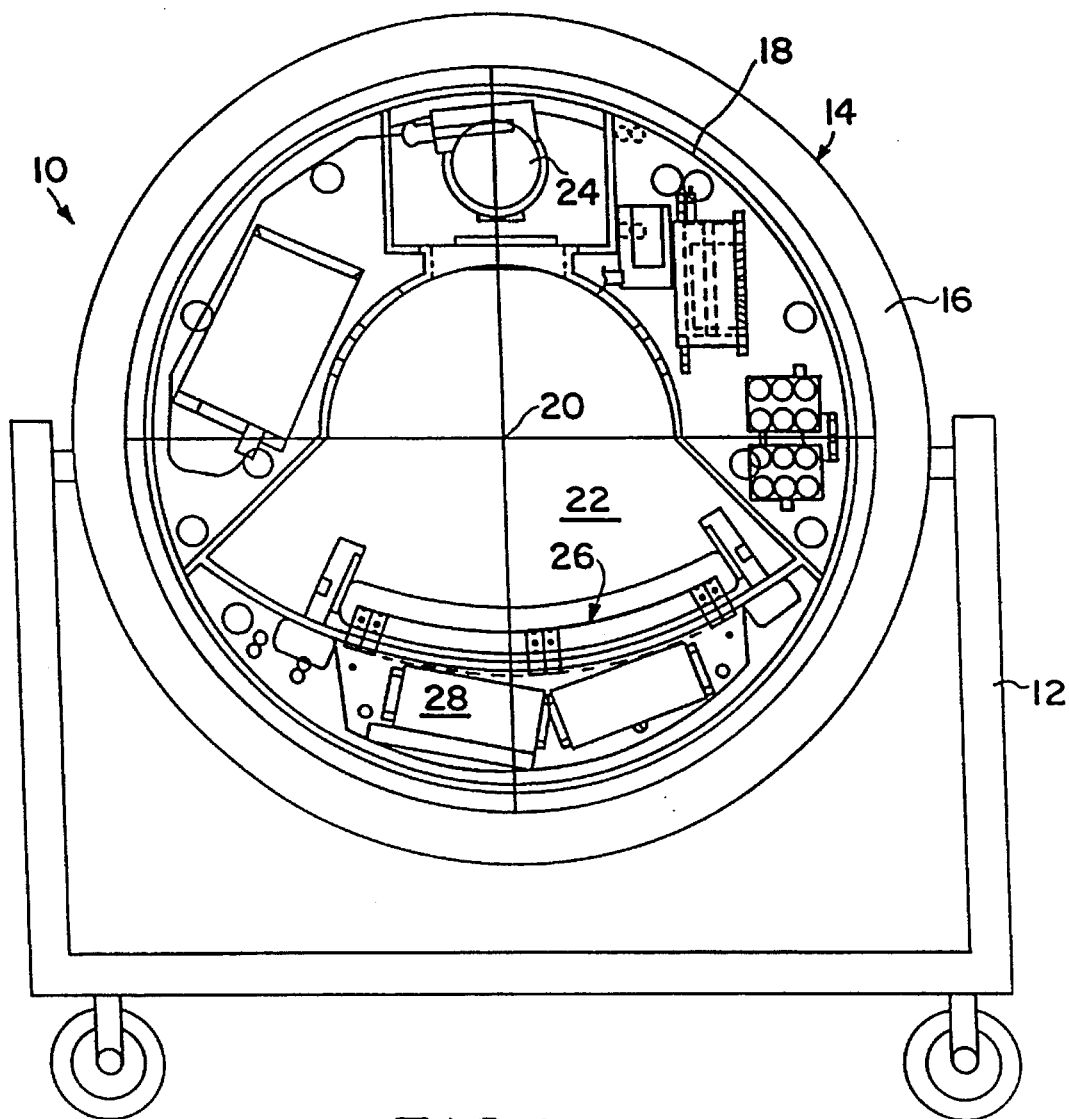
FIG. 1 is an axial view of a CT scanner which can benefit from the present invention.

Referring to FIG. 1, the illustrated CT scanner 10 is of the type more fully described in U.S. patent application Ser. No. 08/193,696, now abandoned entitled Tomographic Scanner Having Center of Rotation for All Physics, filed Feb. 8, 1994 in the names of Ronald E. Swain and Gilbert W. McKenna and assigned to the present assignee. The CT scanner 10 includes a cart 12 for supporting a gantry 14. The gantry 14 includes an annular frame 16 for rotatably supporting an annular disk 18, about a rotation axis 20. The central opening 22 of disk 18 is large enough to receive a patient upon whom a scan is performed.

An X-ray tube 24 is positioned on one side of the disk diametrically across from a detector assembly 26 comprising an array of detectors. A data acquisition system (DAS) 28 is also mounted on the disk 18 for receiving signals from the detector assembly 26.

Figure 2:
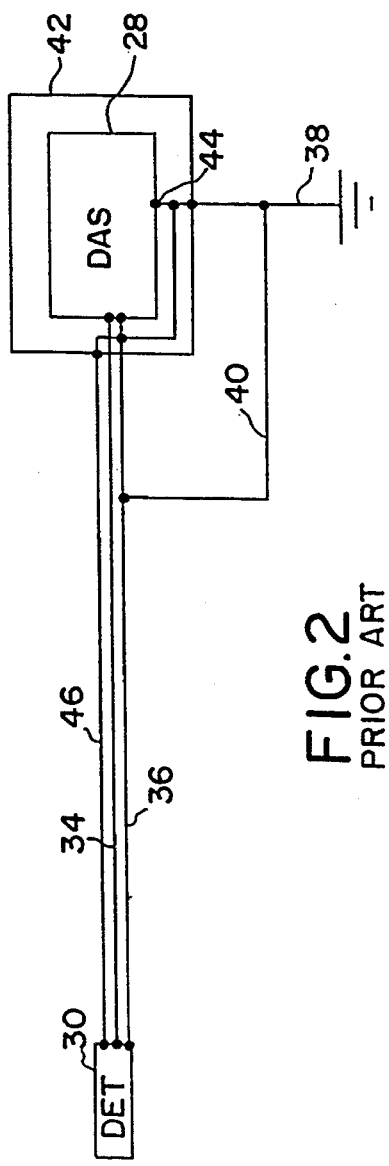
FIG. 2 is a simplified schematic diagram of an x-ray detector assembly connected to a data acquisition system (DAS) shielded and grounded according to the prior art.

With reference to FIG. 2, in accordance with the prior art arrangement a representative x-ray detector 30 of the detector assembly 26 (shown in FIG. 1) is connected to a DAS 28 via a signal line 34 and a return line 36. The detector assembly is of the type that provides relatively low level signals, such as a semiconductor x-ray detector of the type having a crystal portion for converting x-ray photons into visible light photons, and a photodetector portion for converting visible light photons into electrical currents. Each detector 30 of the detector assembly and the DAS 28 must be grounded. It is known to connect the return line 36 of the detector 30 via a system ground line 40 to the system ground 38, formed by the ground plane of the DAS 28, indicated at 44. It is also known to electrostatically shield the DAS 28 with an electrostatic shield 42. The shield 42 is also connected to the DAS ground plane 44 forming system ground 38 in order to maintain the shield 42 at the same potential as the system ground 38. The DAS 28 is substantially enclosed by the shield 42, which creates a "Faraday cage" effect, wherein the electrical components within the shield will be unaffected by any externally generated electric field produced outside the shield 42.

The detector 30 is disposed outside of the shield 42 because, in applications such as a CT scanner, it is either not possible or not desirable to include the detector array inside the shield 42. The signal and return lines 34 and 36 are extended to allow the detector to be remotely positioned with respect to the DAS 28. To electrically shield the lines 34 and 36, a ground plane 46, such as typically found in a stripline cable, is often disposed sufficiently close to the lines 34 and 36, and as shown in contact with the return line 36, so as to provide a shielding effect along their length. Additionally, the ground plane 46 is connected to the DAS ground 44 to maintain the ground plane 46 at the same potential as the DAS ground 44.

However, as shown in FIG. 2, the x-ray detector 30 is particularly sensitive and vulnerable to microphonics, pickup, and other forms of electrical interference. This is particularly true for x-ray detectors of a CT scanner, where highly sensitive x-ray detectors are typically employed.

As a result the return line 36 can be noisy, having voltage fluctuations on the order of millivolts. Thus, even though the detector 30 is connected via the return line 36 and the system ground line 40 to the system ground 38, the noise associated with microphonics and pickup creates inaccuracies in the signals received by the DAS 28.

Figure 3:
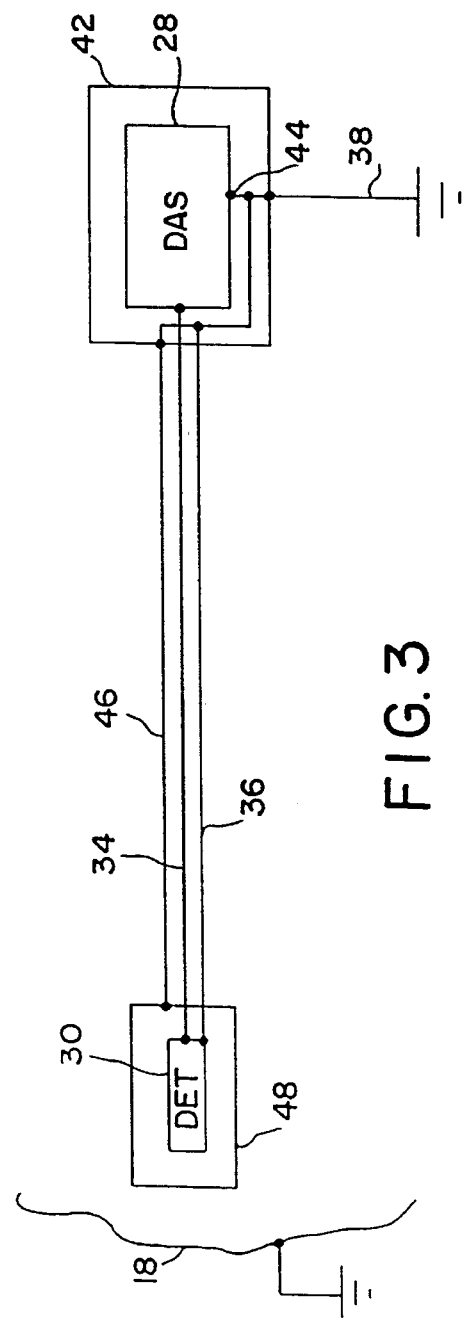
FIG. 3 is a simplified schematic diagram of an x-ray detector assembly connected to a data acquisition system (DAS) shielded and grounded according to the present invention, where in general there will be surfaces which are grounded locally, but which are subject to voltage fluctuations with respect to DAS ground because of relatively large ground currents.

According to the present invention, and illustrated schematically in FIG. 3, an electrostatic shield in the form of an electrically conductive enclosure 48, is employed to provide a Faraday cage or shield so as define a volume where any electric fields external to the shield will have no effect on the detector 30 disposed within the shield. While made of an electrically conductive material the enclosure must be substantially transparent to X-rays, absorbing as few photons as possible so as to have little or no affect on the x-ray measurements made by the detector array. The electrically conductive enclosure 48 is connected to the ground plane 46 so that the shield enclosure 48 is not connected directly to the return line 36 and is independently connected to the DAS ground plane 44. Thus, in FIG. 3 the shields 42 and 48 can be viewed as effectively enclosing the detector 30 as well as the DAS 28, both connected to the DAS ground plane 44, independently of the return line 36. The shields 42 and 48 and the plane 44 are all at the same potential so that there are no field gradients inside or near these surfaces.

Tiny motions of the detector 30 with respect to its environment, which may exhibit a potential gradient, could cause significant signals to be transmitted to the DAS 28, in a phenomenon referred to as "microphonics" if there were no shield 48. Due to the presence of shield 48, such motions will cause charge to flow in the outer surface of the shield enclosure 48 and ground plane 46, without affecting the return and signal lines 34 and 36, and thus without affecting the input to the DAS 28. The conducting enclosure 48 of the invention and its independent connection to the DAS ground plane substantially eliminates microphonics by eliminating any variations in potential that may be encountered by the detector 30 as it moves relative to its local environment. Also, fluctuations in the external ambient electric fields have no affect on the environment inside the enclosure 48, since these fluctuations induce currents on the outside surface of the enclosure 48 that induce fields that cancel everywhere within the volume defined by the enclosure 48.

The enclosure 48 is commonly referred to as a "Faraday cage" or a "Faraday shield". The enclosure 48 can be formed of any electrically conductive material, substantially transparent to X-rays and preferably opaque to light, such as a metal sheet, a metal foil, a metal film, a wire mesh, a network of parallel conductors, or any combination thereof.

Figure 4:
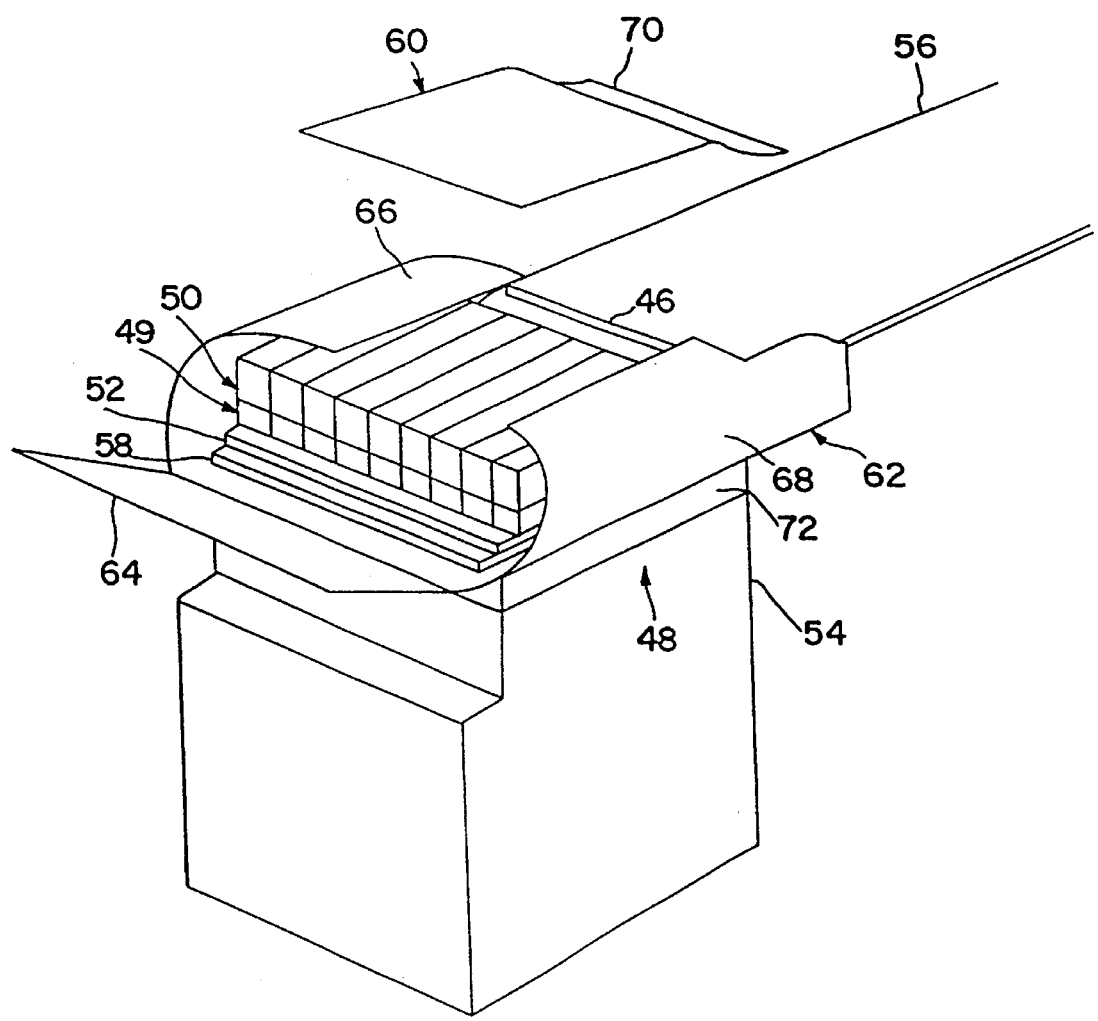
FIG. 4 is a perspective view of an x-ray detector assembly supported on a mounting block showing a partially assembled electrically conductive enclosure.

Referring to FIG. 4, a perspective view is provided of an array of scintillator crystals 50 mounted on an array of semiconductor detectors 49 disposed on a substrate 58, and more fully described in U.S. patent application Ser. No. 08/190,945, entitled "Modular Detector Arrangement for X-ray Tomographic System", filed Feb. 3, 1994 in the names of John Dobbs and David Banks, and assigned to the present assignee (Attorney's Docket ANA-23). The substrate 58 is disposed on a mounting block 54, which can be made of metal. A multiconductor ribbon 56, such as a stripline cable that includes a ground plane, is connectable using a wire bonding technique to the array of detectors to provide a plurality of respective signal and return lines, as well as the ground plane for shielding the signal and return lines.

With reference to FIG. 4, a ceramic layer 52 is disposed under the diode array 49 and includes wire bonding traces (not shown) for connecting each of the diodes in the diode array 49 to respective signal and return lines within the multiconductor ribbon 56.

In accordance with the present invention, an electrically conductive enclosure 48 substantially surrounds or envelops the detector assemblies 50 and 49. The enclosure 48 includes a top foil element 60 and a bottom foil element 62 having first, second, and third flaps 64, 66, and 68. To illustrate a possible closure sequence for providing the electrically conductive enclosure, the second and third flaps 66 and 68 can be wrapped snugly around and secured to the detector arrays 49 and 50. The first flap 64 can then be folded around the end of the detector arrays 49 and 50 to rest on top of the second and third flaps 66 and 68. Then, the top foil element 60 can be secured to the exposed portions of the first second and third flaps 64, 66, and 68 so as to provide a substantially enclosed region wherein the detector assemblies 49 and 50 dwell. The flap 70 of the top foil element 60 is sealed along its length to the ground plane 46 of the multiconductor ribbon 56, thereby grounding the entire conducting enclosure 48. Thus, a conducting enclosure 48 is formed that provides substantially complete electrostatic shielding of the crystal array 50 and diode array 49.

It is well known to shield the x-ray photodetectors from ambient light. Thus, in addition to providing excellent electrostatic shielding, when metal foil, metal sheeting, or metal film is used, the electrically conductive enclosure 48 also provides substantial light shielding that protects the photodetectors in the x-ray detector array 49 from ambient light, further reducing detector signal degradation. In addition, by using a thin layer of aluminum foil, the electrically conductive shield is substantially transparent to X-rays.

Since voltage fluctuations of the mounting structure 54 can subject the detector array 50 to undesirable pickup, the electrically conductive enclosure 48 is electrically isolated from the mounting structure 54 by an electrical insulation layer 72, such as a layer of a dielectric material. For example, a suitable dielectric material is epoxy-impregnated fiberglass, which can provide the requisite insulation as a layer that is one hundredth of an inch thick. Thus, no electrical connection is made from the detector array 50 through the conducting enclosure 48 to the mounting structure 54.

Thus, according to the invention, by shielding the detectors and separately connecting the return line 36 of the detector 30 and the shield 48 to the ground plane 44, without connecting the two together elsewhere, dramatic improvement can be obtained providing signals from the detector 30 to the DAS 28 substantially independent of noise sources attributed to microphonics and pickup.

Thus, the invention provides surprising insensitivity to ambient pickup, microphonics, and system ground voltage fluctuations. For example, large switching power supplies can be disposed in close proximity to the detector array 50 with little deleterious effect.

Other modifications and implementations will occur to those skilled in the art without departing from the spirit and the scope of the invention as claimed. Accordingly, the above description is not intended to limit the invention except as indicated in the following claims.

What is claimed is:

1. An apparatus for shielding and grounding an x-ray detector assembly, wherein the x-ray detector assembly is supported by a mounting structure, and the x-ray detector assembly is electrically connected to a data acquisition system (DAS) via at least a signal line and a return line, the DAS having a ground plane defining system ground, the apparatus comprising:

an electrically conductive enclosure substantially enclosing the x-ray detector assembly; and means for electrically connecting said electrically conductive enclosure to said ground plane independently of said signal line and said return line.

2. Apparatus according to claim 1, wherein the conductive enclosure includes a wire mesh.

3. Apparatus according to claim 1, wherein the conductive enclosure includes a metal film.

4. Apparatus according to claim 1, wherein the conductive enclosure includes metal foil.

5. Apparatus according to claim 1, wherein the conductive enclosure is substantially electrically isolated from the mounting structure.

6. Apparatus according to claim 1, further including an electrical insulation layer interposed between the conductive enclosure and the mounting structure.

7. Apparatus according to claim 6, wherein the electrical insulation layer includes fiberglass impregnated with a resin.

8. Apparatus according to claim 1, wherein the return line is also connected to the DAS ground plane.

9. Apparatus according to claim 1, further including means, electrically connected to said DAS ground plane, for electrically shielding said DAS.

10. Apparatus according to claim 1, wherein said electrically conductive enclosure substantially enclosing the x-ray detector assembly includes a material substantially opaque to ambient light and transparent to x-rays.

11. ACT scanner of the type including (a) a gantry comprising (1) a disk for supporting at least an x-ray source and (2) a frame for rotatably supporting the disk for rotation about a rotation axis, (b) an x-ray detector assembly having (i) at least one x-ray detector cooperative with the at least one x-ray source and (ii) a mounting structure connected to the disk for supporting said at least one detector, and (c) a data acquisition system (DAS) for processing signals received from said at least one detector, wherein the at least one x-ray detector is connected to the DAS by at least a signal line and a return line, the DAS having a ground plane defining system ground, the apparatus further comprising:

an electrically conductive enclosure substantially enclosing the x-ray detector assembly; and means for electrically connecting said electrically conductive enclosure to said ground plane independently of said signal line and said return line.

12. A CT scanner according to claim 11, wherein the conductive enclosure includes a wire mesh.

13. A CT scanner according to claim 11, wherein the conductive enclosure includes a metal film.

14. A CT scanner according to claim 11, wherein the conductive enclosure includes metal foil.

15. A CT scanner according to claim 11, wherein the conductive enclosure is substantially electrically isolated from the mounting structure.

16. A CT scanner according to claim 11, further including an electrical insulation layer interposed between the conductive enclosure and the mounting structure.

17. A CT scanner according to claim 16, wherein the electrical insulation layer includes fiberglass impregnated with a resin.

18. A CT scanner according to claim 11, wherein the return line is also connected to the DAS ground plane.

19. A CT scanner according to claim 11, further including means, electrically connected to said DAS ground plane, for electrically shielding said DAS.

20. A CT scanner according to claim 11, wherein said electrically conductive enclosure substantially enclosing the x-ray detector assembly includes a material substantially opaque to ambient light and transparent to x-rays.

* * * * *